(12) United States Patent
Best et al.

(10) Patent No.: US 10,842,659 B2
(45) Date of Patent: Nov. 24, 2020

(54) KNEE BRACE DEVICE, SYSTEMS, AND METHODS

(71) Applicant: SHOCK DOCTOR, INC., Fountain Valley, CA (US)

(72) Inventors: William Best, Fountain Valley, CA (US); Thierry Petelle, Montreal (CA)

(73) Assignee: SHOCK DOCTOR, INC., Fountain Valley, CA (US)

( * ) Notice: Subject to any disclaimer, the term of this patent is extended or adjusted under 35 U.S.C. 154(b) by 0 days.

(21) Appl. No.: 15/805,529

(22) Filed: Nov. 7, 2017

(65) Prior Publication Data
US 2018/0125693 A1 May 10, 2018

Related U.S. Application Data

(60) Provisional application No. 62/418,592, filed on Nov. 7, 2016.

(51) Int. Cl.
*A61F 5/01* (2006.01)

(52) U.S. Cl.
CPC .......... *A61F 5/0123* (2013.01); *A61F 5/0109* (2013.01); *A61F 2005/0176* (2013.01)

(58) Field of Classification Search
CPC .... A61F 5/0106; A61F 5/0109; A61F 5/0123; A61F 5/0104; A61F 5/0125; A61F 5/01; A61F 2005/0176; A61F 2005/0172; A61F 2005/0174; A41D 13/065; A63B 2071/125
See application file for complete search history.

(56) References Cited

U.S. PATENT DOCUMENTS

| | | | |
|---|---|---|---|
| 4,296,744 A * | 10/1981 | Palumbo | A61F 13/062 2/24 |
| 4,366,813 A | 1/1983 | Nelson | |
| 4,370,978 A | 2/1983 | Palumbo | |
| 6,080,124 A | 6/2000 | Falk et al. | |
| 2004/0153017 A1 | 8/2004 | Simmons et al. | |
| 2005/0020951 A1 | 1/2005 | Gaylord et al. | |
| 2005/0203455 A1* | 9/2005 | Cropper | A61F 5/0123 602/26 |
| 2015/0038891 A1 | 2/2015 | Lipton et al. | |

(Continued)

OTHER PUBLICATIONS

International Preliminary Report on Patentability issued in PCT/US2016/051077, dated Mar. 22, 2018, 6 pages.

(Continued)

*Primary Examiner* — Kari K Rodriquez
(74) *Attorney, Agent, or Firm* — Faegre Drinker Biddle & Reath LLP

(57) ABSTRACT

A knee brace assembly comprising a sleeve and a buttress attached to the sleeve and configured to be positioned against a knee of the wearer. The buttress is configured to be positioned proximate a patella of the wearer and configured to provide support to the patella of the wearer. The knee brace includes a wrap having a first end defining an upper tab and lower tab, and a second end defining an upper and lower tab. The wrap is sized to extend around the leg of the wearer. The upper tab of the first end is configured to attach to the upper tab of the second end, and the lower tab of the first end is configured to attach to the lower tab of the second end, such that the wrap is operable to form a compressive fit around the sleeve and buttress.

21 Claims, 10 Drawing Sheets

(56) References Cited

U.S. PATENT DOCUMENTS

2015/0290014 A1* 10/2015 Anglada ............... A61F 5/0109
                                                    602/26
2015/0374531 A1    12/2015 Fedon

OTHER PUBLICATIONS

International Search Report and Written Opinion issued in PCT/US2016/051077, dated Nov. 4, 2016, 9 pages.
International Search Report and Written Opinion issued in PCT/US2017/060315, dated Feb. 6, 2018, 12 pages.

* cited by examiner

KNEE BRACE DEVICE, SYSTEMS, AND METHODS

CROSS REFERENCE TO RELATED APPLICATION

The present application claims the benefit of and priority to, under 35 U.S.C. § 119(e), U.S. Provisional Application Ser. No. 62/418,592, filed on Nov. 7, 2016, which is hereby incorporated herein by reference in its entirety for all that it teaches and for all purposes.

TECHNICAL FIELD

The instant disclosure relates to devices and methods for supporting a limb or limbs of a user when worn. More specifically, the instant disclosure relates to devices, systems, and methods for supporting a knee of a user when worn.

BACKGROUND

Devices for supporting or stabilizing the limb or limbs of a wearer may be worn by a user for everyday use and/or for use when engaging in physical activity. Injuries to a limb or limbs are common and may affect a user's physical ability and/or athletic performance. For certain users it may be beneficial to use an artificial structure to support a limb that has been weakened or injured. Certain rigid or flexible structures may be worn through the day and/or when engaging in physical activity to provide structural support, or prevent injury. In certain instances they may assist a wearer's movement, reduce weight bearing forces, or provide easier movement capability to a wearer.

For example, an athletic sleeve may be worn around a wearer's limb to provide compression to the limb. An athletic sleeve may also be worn around a wearer's joint such as a knee, wrist, ankle, or elbow to provide lateral or torsional support to the joint and/or to hold the joint in alignment. In some cases, an athletic sleeve may hold snugly to a joint such as a knee or elbow and improve performance while the wearer is engaged in physical activity. However, in some cases, an athletic sleeve may not provide adequate support to a wearer who has suffered an injury or may not provide targeted support to a wearer whose joint may require support in a specific location.

Certain support structures for the leg or knee of a user, such as sleeves, straps, or braces, are available and may provide certain advantages such as agility, comfort, or weight bearing capabilities. Certain rigid devices such as braces with a rigid structure may be uncomfortable or unsuited for use in certain physical activity that requires a particular level of agility or movement by the user's limbs. There is thus a need for a device or method for supporting a limb or limbs of a user that provides suitable weight bearing capability yet is flexible and comfortable enough to be used during physical activity and is also cost effective and accessible.

SUMMARY

Disclosed herein is a knee brace assembly comprising a sleeve having a first end, a second end, and a sleeve length in between the first and second end, the first end defining a first opening configured to receive a leg of a wearer, the second end defining a second opening. The knee brace includes a buttress attached to the sleeve and configured to be positioned against a knee of the wearer. The buttress is configured to be positioned proximate a patella of the wearer and configured to provide support to the patella of the wearer. The knee brace includes a wrap having a first end defining an upper tab and lower tab, and a second end defining an upper and lower tab. The wrap is sized to extend around the leg of the wearer. The upper tab of the first end is configured to attach to the upper tab of the second end, and the lower tab of the first end is configured to attach to the lower tab of the second end, such that the wrap is operable to form a compressive fit around the sleeve and buttress and maintain the buttress against the patella of the wearer when in use.

Also disclosed herein is a knee brace for supporting a patella of a user. The knee brace comprises an inner support member configured to be disposed about a leg of the user. The inner support member includes a sleeve having a first end, a second end, and an inner diameter sized to receive a knee of the user when worn. The knee brace includes a buttress configured to be positioned adjacent the patella of the user by the sleeve when worn. The knee brace further includes an outer support member configured to be positioned around the inner support member and provide compression to the knee of the user when in use. The outer support member includes first and second substantially semicircular ends. The first and second substantially semicircular ends attach to define a circular shape that operates to compress the buttress against the patella of a user when worn.

Also disclosed herein is a knee support system comprising an inner support member comprising a primary support element. The primary support element forms a patella support configured to be positioned proximate a patella of a user and provide support to the patella of the user when worn. The primary support element maintains the patella support against the patella of a user and inhibits movement of the patella in relation to the femur of a user. The knee brace includes an outer support member having a first end defining an upper tab and lower tab, a second end defining an upper and lower tab, and a length configured to extend around a leg of the user when worn. The upper tab of the first end is configured to attach to the upper tab of the second end. The lower tab of the first end is configured to attach to the lower tab of the second end. The wrap first end and second end define a secondary support element configured to form an integrated support with the primary support element to support the patella of the user when worn.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

DETAILED DESCRIPTION

Various aspects of the present disclosure relate to a knee brace that may be worn to protect and/or support a wearer's limb, including a joint, for example a wearer's knee. The support assembly may apply tension and/or compression to the wearer's limb and/or the joint. In some embodiments, the support assembly is shaped and/or contoured to fit and support the knee, or any joint that has suffered an injury. In some embodiments, the knee brace may provide a support system for a wearer who has suffered a meniscus tear, a patella injury, or has an unstable ligament, or an injury affecting lateral or torsional stability.

Figure 1:
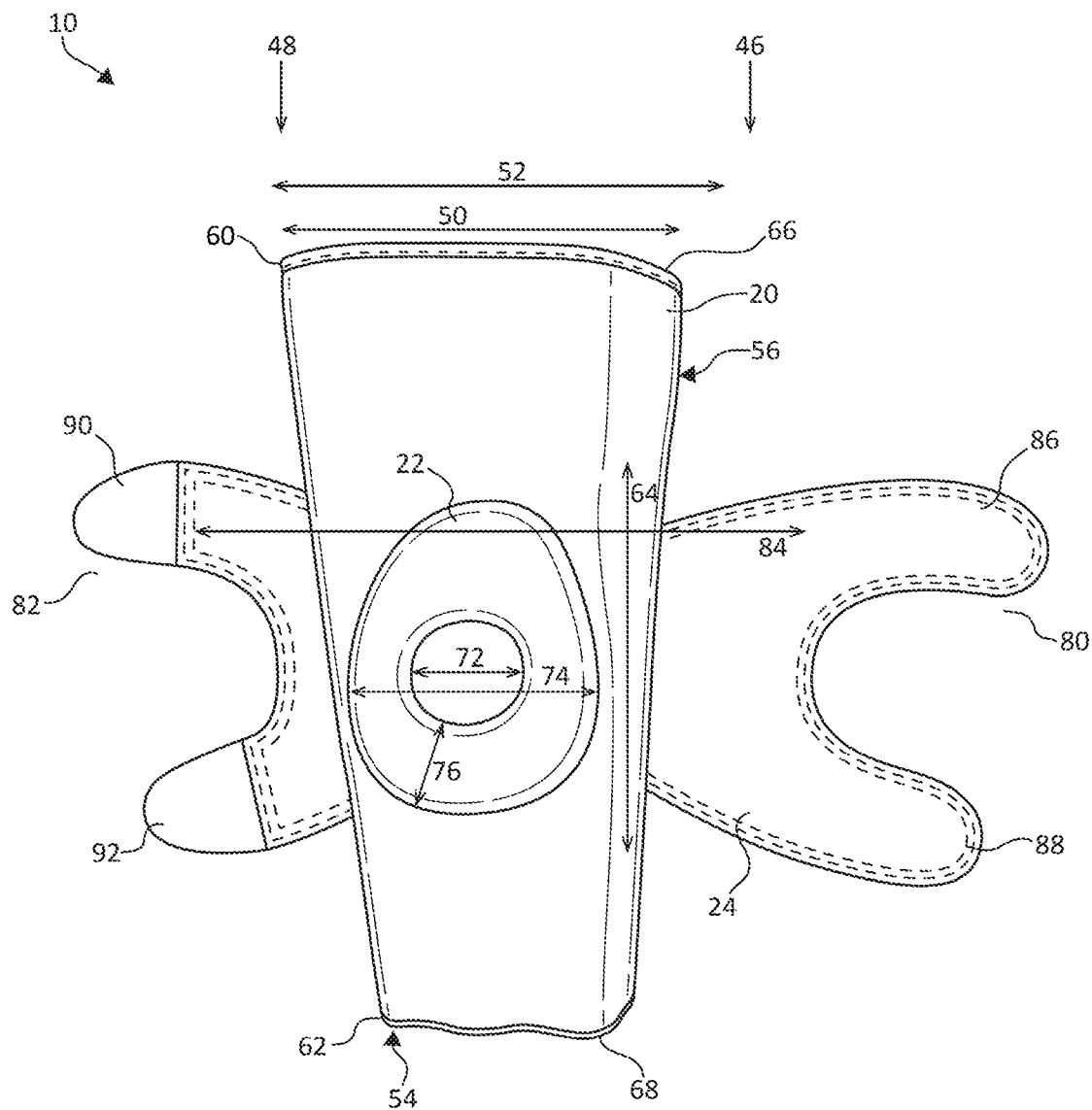
FIG. 1 is a perspective view of an exemplary knee brace.

FIG. 1 is a front view of the knee brace in an open configuration. As shown in FIG. 1, the knee brace 10 includes a sleeve 20, a buttress 22, and a wrap 24.

As shown in FIG. 1, the sleeve 20 may be generally tubular or cylindrical in shape and have a first side 46 and second side 48. The sleeve 20 may define an inner diameter 50, an outer diameter 52, an inner surface 54, and an outer surface 56. The sleeve 20 has a first end 60, a second end 62, and a length 64 in between. The first end 60 defines a first opening 66 and the second end 62 defines a second opening 68. The inner diameter 50 of the sleeve 20 may vary along the length 64 of the sleeve 20. For example, the inner diameter 50 of the sleeve 20 proximate the first end 60 may be sized to receive a portion of the upper leg of a user, such as a thigh, when worn. The inner diameter 50 of the sleeve 20 proximate the second end 62 may be sized to receive the lower leg of a user, such as a calf or shin of a user when worn.

In various embodiments, the sleeve 20 may be constructed so as to be elastic and pliable and thereby fit snugly and provide compression to a user's leg when worn, and further to flex and move with the user's leg when the user runs, jumps or engages in other physical activity while maintaining the aforementioned snug fit at a suitable position on the leg. In various embodiments, the sleeve 20 may operate to wick sweat or other fluids away from a user's leg when worn. In various embodiments, the sleeve 20 may also be configured to have odor absorbing or odor prevention and/or anti-bacterial properties. In some embodiments, the sleeve 20 may have a suitable contour or shape to fit either a user's left leg or right leg. In some embodiments, the sleeve 20 may be a universal sleeve or interchangeable, i.e. the sleeve 20 may be configured to be worn on either a user's left leg or right leg.

The sleeve 20 may be formed using any conventional or later-developed fabrication techniques. In various embodiments, for example, the sleeve 20 may comprise a woven or knit fabric, or may be constructed using any other technique suitable for forming flexible fabric materials.

The material(s) used to form the sleeve 20 can be chosen from any natural or synthetic classes of materials that provide the requisite flexibility, resiliency and manufacturability. In various embodiments, the sleeve 20 may be formed from synthetic elastic materials such as spandex, a polyester-polyurethane copolymer (commonly sold under the brand name Lycra®), or other comparable elastic material. In one embodiment, all or part of the sleeve 20 can include synthetic rubbers such as neoprene. In some embodiments, a material that provides breathability, ventilation, and/or moisture wicking capability may be used. In some embodiments, the sleeve 20 may include a knit nylon or polyester material. In some embodiments, the sleeve 20 may include a perforated material. In various embodiments, a plurality of different materials is used to construct the sleeve 20.

As shown in FIG. 1, in some embodiments, the buttress 22 is shaped generally as an annular, or substantially annular, structure defining an inner diameter 72, and an outer diameter 74. The buttress 22 may have a width 76 that is defined as the distance between the outer diameter 74 and the inner diameter 72. The buttress 22 may also have a thickness as measured in a direction normal to a direction of the width. In some embodiments, the width 76 may be greater than the thickness, and the buttress 22 may resemble a disk with an opening in the center. In some embodiments, the width 76 of the buttress 22 may be substantially the same as the thickness, and the buttress 22 may have a shape resembling a donut or torus. In some embodiments, the buttress 22 may resemble a donut or torus in a first plane. In various embodiments, the buttress 22 may be a substantially continuous annular structure. In other embodiments, the buttress 22 may be composed of a plurality of semi-annular segments that are arranged so as to form a substantially annular shape.

In some embodiments, the buttress 22 may be formed as one or more C-shaped pads optionally shaped to support various joint injuries and can be provided with a unique design and shape for a variety of injuries.

The buttress 22 may be constructed to be overall compliant or flexible, and allow the buttress 22 to bend or conform to a suitable shape. For example, the buttress 22 may be constructed from material that provides a resilient yet pliable support that can be shaped to contour to the outer surface of a user's leg when worn. The buttress 22 may be made of material that absorbs force or shock directed at the leg or knee of a user. The buttress 22 may include material such as rubber, silicone, plastic, foam, or any pliable material that may be used as cushioning or padding. The buttress may be formed from a material molded into a suitable shape or size, such as molded silicon or rubber. The buttress 22 may include a tube that may be filled with air for cushioning, and the buttress 22 may be adjusted by varying a pressure of air inside the tube. The buttress 22 may include a tube filled with fluid or gel material, for example gel contained with a bag or tube that forms the overall shape of the buttress 22.

The buttress 22 may be sized and shaped to form a suitable complementary fit with the leg of a user. For example, the features of the buttress 22 may be shaped to conform to the leg and/or patella of a user when worn. The buttress 22 may be flexible to conform to the sleeve 20, and the buttress 22 may bend out of plane with the first plane to conform to the outside surface of a user's leg when worn. In some embodiments, the outer diameter 74 of the buttress 22 may be large enough to cover the width of the front of a user's leg when worn. In some embodiments, the outer diameter 74 of the buttress 22 may be smaller than the width of the front of a user's leg, but wider than the width of the user's patella.

In some embodiments, the buttress 22 may have a suitable shape to provide support to the patella of a user when worn. For example, when worn, the sleeve 20 may position the buttress 22 against the outside surface of the leg of a user. The buttress 22 may be made of flexible material that can be shaped or stretched to generally conform to the outside surface of a user's knee, and the inner diameter 72 of the buttress 22 may be sized to receive and/or surround and bear against at least a portion of the patella of a user when worn.

For example, the sleeve 20 may provide compressive forces to the leg of a user when worn and maintain the buttress 22 in position along the front of the patella and around the circumference of the patella of a user in the frontal plane of the user's body. The combination of the sleeve 20 and buttress 22 may be used to maintain a support structure around and in front of the patella of a user and provide comfortable support to the patella when worn by a user.

In some embodiments, the inner diameter 72 of the buttress 22 may be sized so as to have a complementary fit to the outer circumference of the patella of a user when worn. For example, the inner diameter 72 may be sized to allow a user to position his or her patella with the first plane of the buttress 22 in a parallel plane as the frontal plane of his or her body. The inner diameter 72 of the buttress 22 may be suitably sized to conform substantially to an outer circumference of the patella, and, using the compressive force of the sleeve 20, the buttress 22 may be curved in relation to the first plane to conform to the outer surface of the user's leg. In some embodiments, the sleeve 20 maintains the buttress 22 in position against the patella of a user and inhibits movement of the patella in relation to the femur of a user. In some embodiments, the sleeve 20 maintains the buttress 22 in position against the patella of a user and inhibits movement of the patella in relation to the tibia of a user. In some embodiments, the sleeve 20 maintains the buttress 22 in position against the patella of a user and inhibits movement of the patella in axial or longitudinal relation to the leg of a user.

In some embodiments, the generally annular shape of the buttress 22 allows the buttress 22 to surround the patella of a user when worn yet provides a flexible and pliable support that moves with the leg or knee of a wearer. In various embodiments, the buttress 22 may be capable of bending out of the first plane without creasing along the surface of the patella. In some embodiments, the shape of the buttress 22 allows the buttress 22 to nestle the patella within the buttress 22 and provide support without exerting stress to the user's leg to maintain the buttress 22 in position around the user's patella. The annular shape also results in the buttress 22 being generally lighter in weight than a continuous pad without a central opening. The opening in the inner diameter 72 of the ring also provides breathability from the knee of a user through the sleeve 20. Thus the annular shape of the buttress 22 provides the buttress 22 with a shape that provides padding and/or support to a user's knee as the user engages in physical activity while reducing stress to the user's leg that may inhibit leg flexing.

As shown in FIG. 1, the buttress 22 may be a separate component attached to the sleeve 20 by any conventional or later-developed attachment technique (e.g., stitching). In some embodiments, the buttress 22 may be integrally formed or interwoven with the sleeve 20 which may provide restraint for keeping the buttress 22 in position along the length 64 of the sleeve 20. The buttress 22 may be positioned between the inner surface 54 and the outer surface 56 of the sleeve 20. In some embodiments, the buttress 22 may be attached to the outer surface of the sleeve 56. That is, the sleeve 20 may be provided, and the buttress 22 may be provided as a separate article to be attached to the inner surface 54 or outer surface 56 of the sleeve 20 using any suitable device or method for attachment such as glue, stitching, a hook and loop material such as that sold under the tradename Velcro®, or any other method of attachment. In some embodiments, the sleeve 20 and buttress 22 in combination form a first supporting member that can be used to provide structural support to a user's knee and/or patella.

That is the sleeve 20 and buttress 22 in combination may form an inner patella support element that may also be referred to as an inner or first support member.

As shown in FIG. 1, the wrap 24 may have a first end 80, a second end 82, and a length 84 in between the first end 80 and the second end 82. The first end 80 may include a first tab 86, and a second tab 88. The second end 82 may include a first tab 90, and a second tab 92. The length 84 may be sized to allow the wrap 24 to extend around the leg of a user. For example, the length 84 may be a suitable size for the wrap 24 to extend in a second plane substantially parallel the transverse plane of the body of the user and allow the first and second ends 80, 82 to meet. The wrap 24 may be configured to form a substantially U-shaped or semicircular shaped support member along the first end 80 or second end 82. For example, the first and second tabs 86, 88 of the first end 80 may be elongated to define a split first end 80 that has a U-shape, C-shape, or semicircular shape. Similarly, the first and second tabs 90, 92 of the second end 82 may be elongated to define a split second end 82 that as a U-shape, C-shape, or semicircular shape.

In some embodiments, the wrap 24 may be formed separate of the sleeve 20. In some embodiments, the wrap 24 may include an elongated structure that forms a portion of the length 84 of the wrap 24 and C-shaped structures attached to each of the ends of the elongated structure to form the tabs 86, 88, 90, 92. In some embodiments, the wrap 24 may be unattached to the sleeve, and forms part of the knee brace 10 by wrapping around the sleeve 20 and the buttress 22 and connecting with itself.

In some embodiments, the wrap 24 may be attached to the sleeve 20. In some embodiments, the wrap 24 may be attached to the sleeve 20 by attaching to the outer surface 56 of the sleeve by stitching, gluing, melt bonding, or any suitable attachment means. In some embodiments, the wrap 24 may be integrally formed with the sleeve 20. In some embodiments, the wrap 24 may be woven through or inserted along the length 64 of the sleeve 20. For example, the sleeve 20 may have slots or openings along the length 64 through which the wrap 24 may be inserted, thus joining with the sleeve 20 to form an integral fit with the sleeve 20. The wrap 24 may be attached to the sleeve 20 at any suitable location. For example the wrap 24 may be attached to sleeve 20 at a location that corresponds to the back of a user's leg when worn. The wrap 24 may be attached to the sleeve 20 that corresponds to the side or sides of a user's leg when worn.

Figure 2:
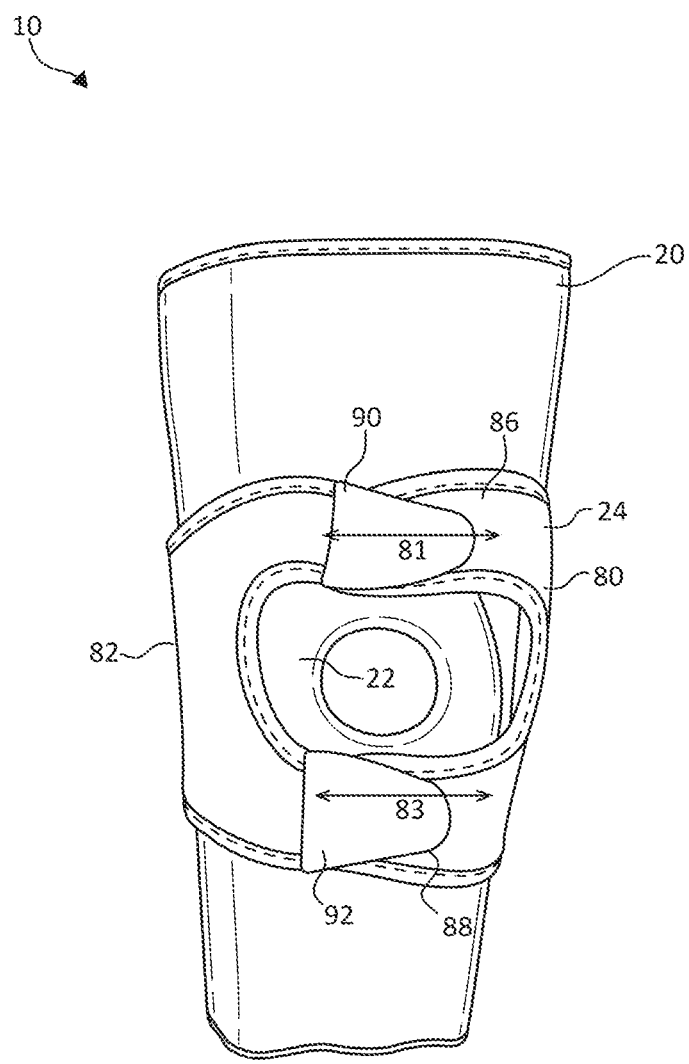
FIG. 2 is a front view of an exemplary knee brace.

FIG. 2 is a front view of the knee brace 10 described with reference to FIG. 1 showing the knee brace 10 in a closed configuration. As shown in FIG. 2, the sleeve 20 may form a first member forming the innermost part of the knee brace 10 closest to a user's leg when worn. In some embodiments, the buttress 22 may be on the inside of the sleeve 20. In some embodiments, the buttress 22 may be on the outside of the sleeve 20. In some embodiments, the sleeve 20 and buttress 22 in combination form a primary or inner support member that can be used to provide support to a user's knee and/or patella. As shown in FIG. 2 the wrap 24 may be configured to attach to itself and form a secondary or outer support member. The wrap 24 may be configured to form a substantially circular or substantially semicircular shape when attached. For example, as shown in FIG. 2, the first tab 86 of the first end 80 may be connected or attached to the first tab 90 of the second end 82 to form an upper strap 81. The second tab 88 of the first end 80 may be connected or attached to the second tab 92 of the second end 82 to form a lower strap 83. In some embodiments, the upper strap 81 may be positioned superior to a user's knee when worn, and the lower strap 83 may be positioned inferior to a user's knee when worn. The upper strap 81 and lower strap 83 of the wrap 24 may form a secondary or outer support member that works in combination with the primary or inner support member to support the knee and/or patella of a user.

In some embodiments, the integration of the wrap 24 with the sleeve 20 provides targeted and adjustable compression and/or support in the area of a user's patella when worn. In some embodiments, the sleeve 20 and the buttress 22 in combination may provide an inner or first support member. The wrap 24 may integrate with the sleeve 20 to provide adjustable, supplemental support to the user's knee when worn. The wrap 24 may be sized and shaped to overlap with the buttress 22 and hold or cradle the buttress 22 in position adjacent a user's knee when worn. For example, the wrap 24 may be sized to cover at least a portion of the buttress 22 from the front of a user's knee with part of the wrap 24 covering around the outside of a the buttress 22. In this configuration, the wrap 24 may push the buttress 22 down over a user's knee along the outer diameter 74 of the buttress 22.

In some embodiments, the sleeve 20 may be used alone without a buttress 22 and the sleeve 20 forms the inner support member. In some embodiments, an inner or first support member may be formed by a sleeve 20 having suitable compression or to provide support to a user's knee without a separate buttress 22. That is, the sleeve 20, and the wrap 24, may work in conjunction to support the patella of a user such that the sleeve 20 forms an inner support member and the wrap 24 forms an outer or secondary support member, and the inner and outer support members provide suitable support to a user's patella. In embodiments both with and without a buttress 22, the shape of the wrap 24 may be used to support a user's knee and provide controllable support to the user's knee.

Figure 3A:
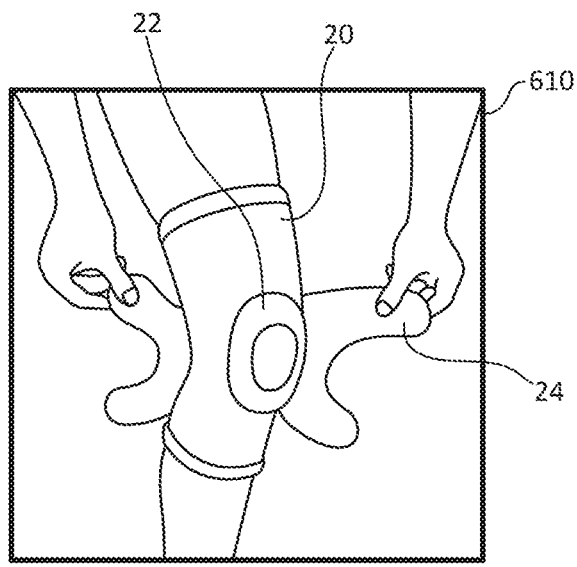
FIGS. 3A-3E are perspective views of the exemplary knee brace of FIGS. 1 and 2 in various stages of fitting on a leg of a wearer.

FIGS. 3A-3E illustrate the knee brace 10 in various exemplary stages of fitting onto a leg of a wearer. As shown in FIG. 3A, in step 610 the sleeve 20 may be placed on a user's knee by inserting the user's leg into the sleeve 20 and advancing the sleeve 20 along the user's leg until it is positioned around the user's knee. The sleeve 20 may be positioned with the buttress 22 adjacent to the user's patella. In step 610, the wrap 24 may also be positioned with at least a portion of the wrap 24 behind the user's knee.

Figure 3B:
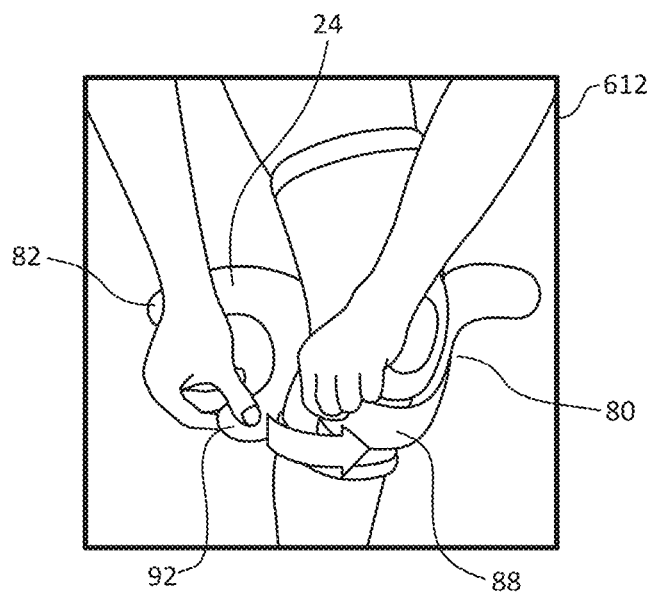

As shown in FIG. 3B, in step 612, the wrap 24 may be positioned around the user's knee with a portion of the wrap 24 behind the user's knee and the first and second ends 80, 82 of the wrap in front of the user's knee. In step 612, the wrap 24 may be fitted around the user's knee by attaching the first end 80 to the second end 82. As shown in FIG. 3B the second tab 88 of the first end 80 may be attached to the second tab 92 of the second end 82. In some embodiments, the wrap 24 may be adjusted for a suitable size or fit by adjusting the tension in the wrap 24.

Figure 3C:
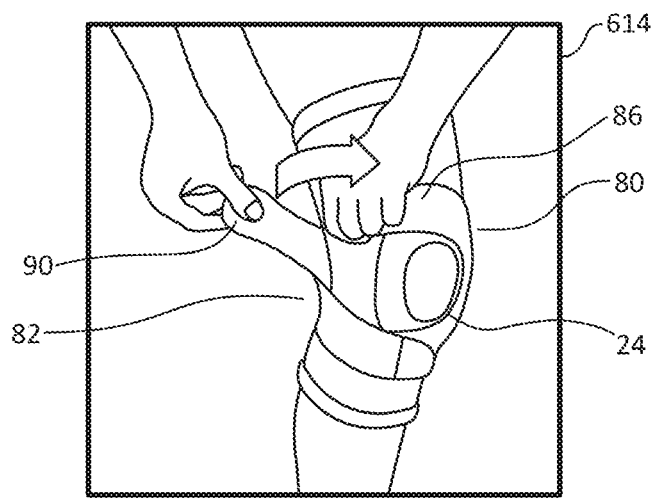

As shown in FIG. 3C, the wrap 24 may be further attached around the user's knee by attaching the first tab 86 of the first end 80 to the first tab 90 of the second end 82 in step 614. The wrap 24 may be adjusted for a suitable size or fit by adjusting the tension in the wrap 24. Note that steps 612 and 614 may be carried out in any suitable order. The tension in the wrap 24 may be readjusted at any time by repositioning the first and second ends 80, 82 in relation to each other.

Figure 3D:
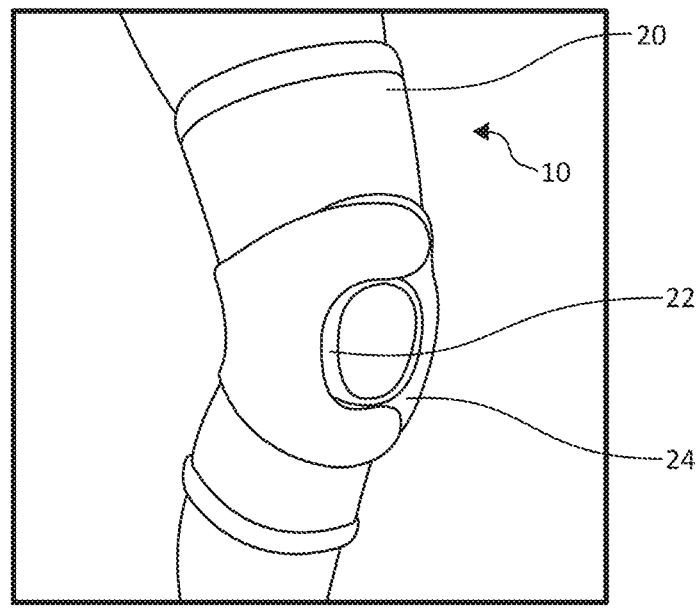
Figure 3E:
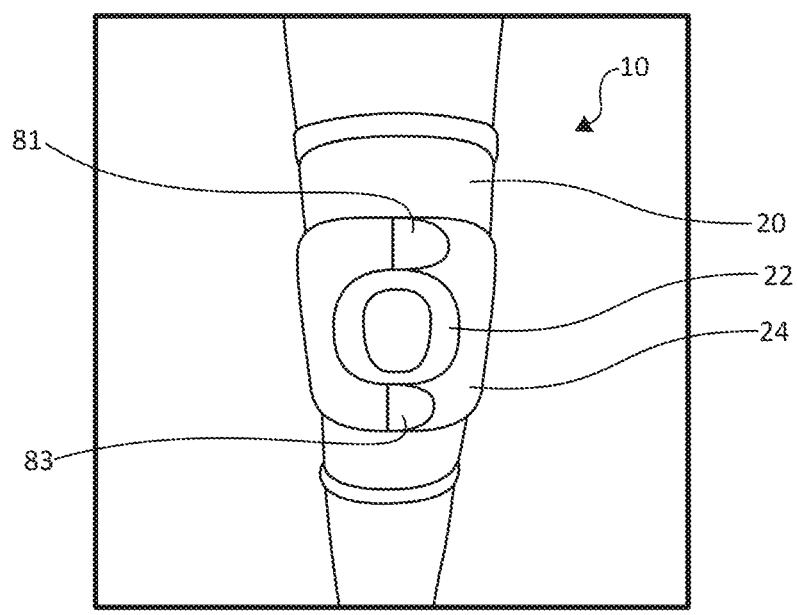

FIG. 3D is a perspective view showing the knee brace 10 in position on a user's knee. The sleeve is positioned on the user's knee and holds the buttress 22 in place adjacent to the user's knee. The wrap 24 is positioned to maintain the buttress 22 in place against the user's knee and provides supplemental support to the sleeve 20 to provide fit and tension to the user's knee. FIG. 3E is a front view showing the knee brace 10 in position on a user's knee. As shown in FIG. 3E, the knee brace 10 may be positioned on a user's knee with the sleeve 20 inside the wrap 24. The sleeve 20 and buttress 22 form an inside support element that forms a primary support element. The wrap 24 is positioned around the sleeve 20 and buttress 22 and provides supplemental support to the user's knee by providing a compressive force inward to the buttress 22 to maintain the buttress 22 against the user's knee. The wrap 24 forms an outside support element that forms a secondary support element to the sleeve 20 and buttress 22. For example, the wrap 24 may form an upper and lower strap 81, 83 that form a circular or semi-circular shape that provides compression to the buttress 22 inward toward a user's patella.

Figure 4:
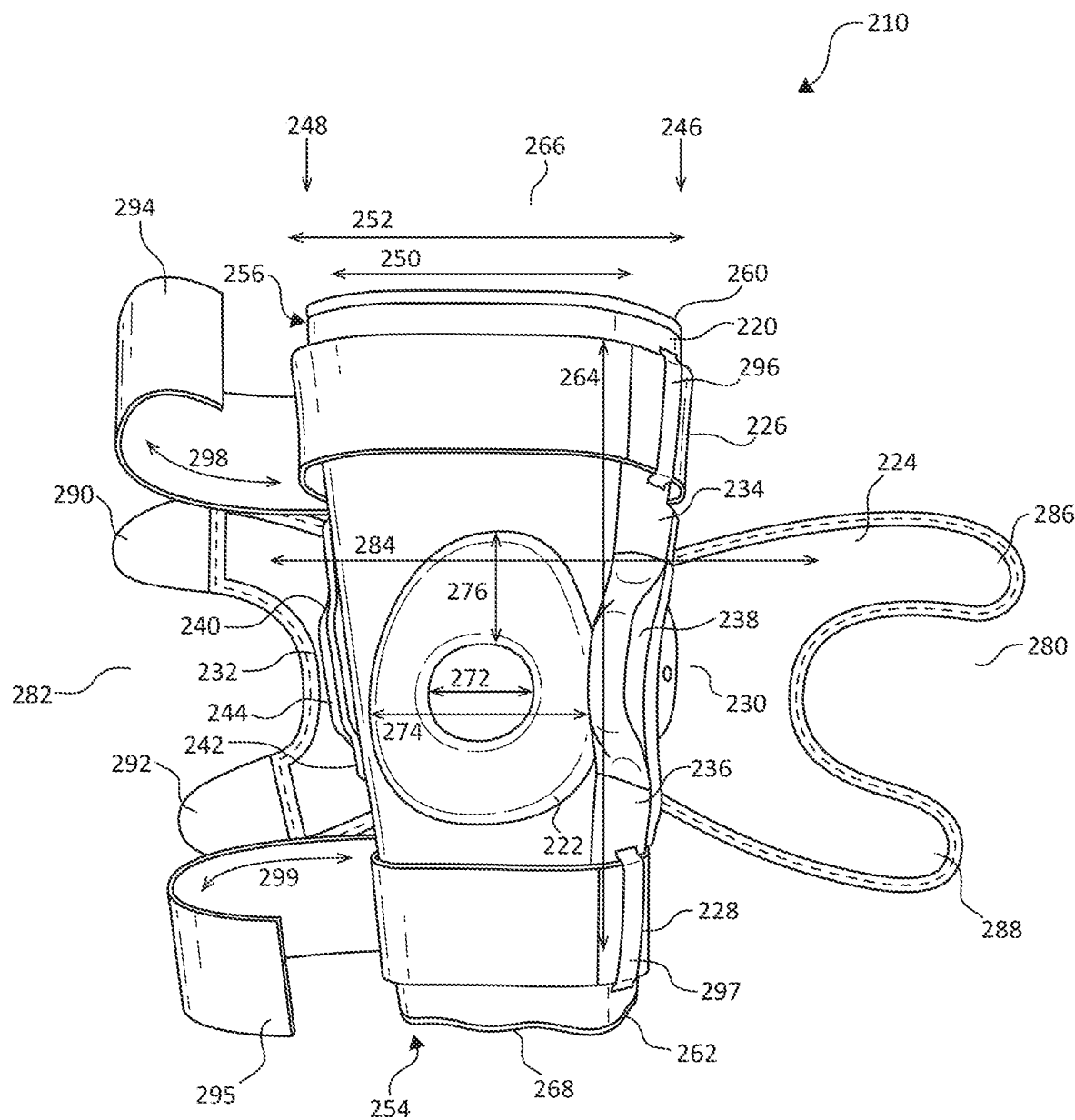
FIG. 4 is a front view of an exemplary knee brace.

FIG. 4 is a front view of an alternative embodiment of a knee brace 210 having a sleeve 220, a buttress 222, and a wrap 224. In some embodiments, the features, materials and methods of construction of the knee brace 210 shown in FIG. 4 are substantially the same or similar to the features described with reference to FIGS. 1 and 2, with similar features beginning with the number 2. As shown in FIG. 4, in some embodiments, the knee brace 210 may also include a first cuff strap 226, a second cuff strap 228, a first brace structure 230, and a second brace structure 232. The first brace structure 230 includes a first upper hinge stay 234, a first lower hinge stay 236, and a first hinge 238. The second brace structure 232 includes a second upper hinge stay 240, a second lower hinge stay 242, and a second hinge 244.

As shown in FIG. 4, the sleeve 220 may be generally tubular or cylindrical in shape and have a first side 246 and second side 248. The sleeve 220 may define an inner diameter 250, an outer diameter 252, an inner surface 254, and an outer surface 256. The sleeve 220 has a first end 260, a second end 262, and a length 264 in between. The first end 260 defines a first opening 266 and the second end 262 defines a second opening 268. The inner diameter 250 of the sleeve 220 may vary along the length 264 of the sleeve 220. For example, the inner diameter 250 of the sleeve 220 proximate the first end 260 may be sized to receive a portion of the upper leg of a user, such as a thigh, when worn. The inner diameter 250 of the sleeve 220 proximate the second end 262 may be sized to receive the lower leg of a user, such as a calf or shin, when worn.

In various embodiments, the sleeve 220 may be constructed so as to be elastic and pliable and thereby fit snugly and provide compression to a user's leg when worn, and further to flex and move with the user's leg when the user runs, jumps or engages in other physical activity while maintaining the aforementioned snug fit at a suitable position on the leg. In various embodiments, the sleeve 220 may operate to wick sweat or other fluids away from a user's leg when worn. In embodiments, the sleeve 220 may also be configured to have odor absorbing or odor prevention and/or anti-bacterial properties. In some embodiments, the sleeve 220 may have a suitable contour or shape to fit either a user's left leg or right leg. In some embodiments, the sleeve 220 may be a universal sleeve or interchangeable, i.e. the sleeve 220 may be configured to be worn on either a user's left leg or right leg.

The sleeve 220 may be formed using any conventional or later-developed fabrication techniques. In various embodiments, for example, the sleeve 220 may comprise a woven or knit fabric, or may be constructed using any other technique suitable for forming flexible fabric materials. For example, the sleeve 220 may include a knit nylon or polyester. A knit material may be used to form a sleeve 220 that is breathable and/or ventilated.

The material(s) used to form the sleeve 220 can be chosen from any natural or synthetic classes of materials that provide the requisite flexibility, resiliency and manufacturability. In various embodiments, the sleeve 220 may be formed from synthetic elastic materials such as spandex, a polyester-polyurethane copolymer (commonly sold under the brand name Lycra®), or other comparable elastic material. In one embodiment, all or part of the sleeve 220 can include synthetic rubbers such as neoprene. In various embodiments, a plurality of different materials is used to construct the sleeve 220. In short, any materials suitable for use in the various components of the sleeve 20 can also be used for the sleeve 220.

As shown in FIG. 4, in some embodiments, the buttress 222 is shaped generally as an annular, or substantially annular, structure defining an inner diameter 272, and an outer diameter 274. The buttress 222 may have a width 276 that is defined as the distance between the outer diameter 274 and the inner diameter 272. The buttress 222 may also have a thickness in the direction normal to the width 276. In some embodiments, the width 276 may be greater than the thickness, and the buttress 222 may resemble a disk with an opening in the center. In some embodiments, the width 276 of the buttress 222 may be substantially the same as the thickness, and the buttress 222 may have a shape resembling a donut or torus. In some embodiments, the buttress 222 may resemble a donut or torus in a first plane. In various embodiments, the buttress 222 may be a substantially continuous annular structure. In other embodiments, the buttress 222 may be composed of a plurality of semi-annular segments that are arranged so as to form a substantially annular shape.

In some embodiments, the buttress 222 may be formed as one or more C-shaped pads optionally shaped to support various joint injuries and can be provided with a unique design and shape for a variety of injuries.

The buttress 222 may be constructed to be overall compliant or flexible, and allow the buttress 222 to bend or conform to a suitable shape. For example, the buttress 222 may be constructed from material that provides a resilient yet pliable support that can be shaped to contour to the outer surface of a user's leg when worn. The buttress 222 may include material such as rubber, plastic, foam, or any pliable material that may be used as cushioning or padding. The buttress 222 may include a fluid or gel material, for example gel contained within a bag or tube that forms the overall shape of the buttress 222. The buttress 222 may be made of material that absorbs force or shock directed at the leg or knee of a user.

The buttress 222 may be sized and shaped to form a suitable complementary fit with the leg of a user. For example, the features of the buttress 222 may be shaped to conform to the leg and/or patella of a user when worn. The buttress 222 may be flexible to conform to the sleeve 220, and the buttress 222 may bend out of plane with the first plane to conform to the outside surface of a user's leg when worn. In some embodiments, the outer diameter 274 of the buttress 222 may be large enough to cover the width of the front of a user's leg when worn. In some embodiments, the outer diameter 274 of the buttress 222 may be smaller than the width of the front of a user's leg, but greater than the width of the user's patella.

In some embodiments, the buttress 222 may have a suitable shape to provide support to the patella of a user when worn. For example, when worn, the sleeve 220 may position the buttress 222 against the outside surface of the leg of a user. The buttress 222 may be made of flexible material that can be shaped or stretched to conform to the outside surface of a user's knee, and the inner diameter 272 of the buttress 222 may be sized to receive at least a portion of the patella of a user when worn. For example, the sleeve 220 may provide compressive forces to the leg of a user when worn and maintain the buttress 222 in position along the front of the patella and around the circumference of the patella of a user in the frontal plane of the user's body. The combination of the sleeve 220 and buttress 222 may be used to maintain a support structure around and in front of the patella of a user and provide comfortable support to the patella when worn by a user.

In some embodiments, the inner diameter 272 of the buttress 222 may be sized with a complementary fit to the outer circumference of the patella of a user when worn. For example, the inner diameter 272 may be sized to allow a user to position his or her patella with the first plane of the buttress 222 in a parallel plane as the frontal plane of his or her body. The inner diameter 272 of the buttress 222 may be suitably sized to conform substantially to an outer circumference of the patella, and using the compressive force of the sleeve 220 the buttress 222 may be curved in relation to the first plane to conform to the outer surface of the user's leg.

As shown in FIG. 4, the buttress 222 may be a separate component attached to the sleeve 220. In some embodiments, the buttress 222 may be integrally formed or interwoven with the sleeve 222 which may provide restraint for keeping the buttress 222 in position along the length 264 of the sleeve 220. The buttress 222 may be positioned between the inner surface 254 and the outer surface 256 of the sleeve 220. In some embodiments, the buttress 222 may be attached to the outer surface of the sleeve 256. That is, the sleeve 220 may be provided as a separate article, and the buttress 222 attached to the inner surface 254 or outer surface 256 of the sleeve 220 using any suitable device or method for attachment such as glue, stitching, a hook and loop material such as that sold under the tradename Velcro®, or any other method of attachment.

In some embodiments, the generally annular shape of the buttress 222 allows the buttress 222 to surround the patella of a user when worn yet provides a flexible and pliable support that moves with the leg or knee of a wearer. For example, the shape of the buttress 222 may allow the buttress 222 to bend out of the first plane without creasing along the surface of the patella. In some embodiments, the torus or donut shape allows the buttress 222 to nestle the patella against the buttress 222 and provide support without exerting stress to the user's leg to maintain the buttress 222 in position around the user's patella. The buttress 222 also allows the buttress to be lighter in weight than a continuous pad. The opening in the inner diameter 272 of the buttress 222 also provides breathability for the knee of a user through the sleeve 220. Thus the torus or donut shape of the buttress 222 provides a buttress 222 that provides padding and/or support to a user's knee as the user engages in physical activity while reducing stress to the user's leg that may inhibit the user's leg from flexing when the knee brace 210 is worn.

As shown in FIG. 4, the wrap 224 may have a first end 280, a second end 282, and a length 284 in between. The first end 280 may include a first tab 286, and a second tab 288. The second end may include a first tab 290, and a second tab 292. The length 284 may be sized to allow the wrap 224 to extend around the leg of a user. For example, the length 284 may be a suitable size for the wrap 224 to extend in a second plane substantially parallel the transverse plane of the body of the user and allow the first and second ends 280, 282 to meet.

In some embodiments, the wrap 224 may be formed separate of the sleeve 220. In some embodiments, the wrap 224 may include an elongated structure that forms a portion of the length 84 of the wrap 24, and C-shaped structures attached to each of the ends of the elongated structure to form the tabs 286, 288, 290, 292. In some embodiments, the wrap 224 may be unattached to the sleeve, and forms part of the knee brace 210 by wrapping around the sleeve 220 and the buttress 222 and connecting with itself.

In some embodiments, the wrap 224 may be attached to the sleeve 220. In some embodiments, the wrap 224 may be attached to the sleeve 220 by attaching to the outer surface 256 of the sleeve by stitching, gluing, melt bonding, or any suitable attachment means. In some embodiments, the wrap 224 may be integrally formed with the sleeve 220. In some embodiments, the wrap 224 may be woven through or inserted along the length 264 of the sleeve 220. For example, the sleeve 220 may have slots or openings along the length 264 through which the wrap 224 may be inserted, thus joining with the sleeve 220 to form an integral fit with the sleeve 220.

In some embodiments, the wrap 224 may be attached to the sleeve 220 at any suitable location. For example the wrap 224 may be attached to sleeve 220 at a location that corresponds to the back of a user's leg when worn. The wrap 224 may be attached to the sleeve 220 that corresponds to the side or sides of a user's leg when worn.

As shown in FIG. 4, the first brace structure 230 may be positioned on the first side 246 of the sleeve 220, and the second brace structure 232 may be positioned on the second side 248 of the sleeve 220. The first upper hinge stay 234 may be attached to the sleeve 220 near the first end 260, the first lower hinge stay 236 may be attached to the sleeve 220 near the second end 262, and the first hinge 238 may attach the first upper hinge stay 234 in hinged relation to the first lower hinge stay 236. The second upper hinge stay 240 may be attached to the sleeve 220 near the first end 260, the second lower hinge stay 242 may be attached to the sleeve 220 near the second end 262, and the second hinge 244 may attach the second upper hinge stay 240 in articulable or hinged relation to the second lower hinge stay 242. In some embodiments, the first and second upper hinge stays 234, 240 may be configured to support the upper leg of a user when worn. The first and second lower hinge stays 236, 242 may be configured to support the lower leg of a user when worn. The first and second hinges 238, 244 may be configured to articulate with a user's knee when worn and support the knee of a user.

In the embodiment of FIG. 4, the first cuff strap 226 may have a first end (not shown in FIG. 4), a second end 294, and a length 298 in between the first end and second end 294. The second cuff strap 228 may have a first end (not shown in FIG. 4), a second end 295, and a length 299 in between the first end and second end 295. The first cuff strap 226 may be positioned along the outside surface 256 of the sleeve 220 and may be used to maintain the first end 260 of the sleeve 220 in position on a user's leg when worn. The second cuff strap 228 may be positioned along the outside surface 256 of the sleeve 220 and may be used to maintain the second end 262 of the sleeve 220 in position on a user's leg when worn. For example, the first cuff strap 226 may be used to maintain a portion of the length 264 of the sleeve 220 adjacent the first end 260 in position along the thigh of a user, and the second cuff strap 228 may be used to maintain a portion of the length 264 of the sleeve 220 adjacent the second end 228 along the calf of a user when worn. The first and second cuff straps 226, 228 may be tensioned to apply a compressive force to the first and second ends 260, 262 of the sleeve 220 respectively.

The first and second cuff straps 226, 228 may be attached to the sleeve 220 along the outside surface 256 using any suitable attachment such as stitching, glue, melt bonding, or a hook and loop fastener such as that sold under the tradename Velcro®. In some embodiments, the first and second cuff strap 226, 228 first ends (hidden from view) may be attached to the sleeve 220, and the lengths 298, 299 of the first and second cuff straps 226, 228 may wrap around the outer surface 256 of the sleeve 220. The second end 294 of first cuff strap 226 may attach to the first cuff strap 226 along the length 298 of the first cuff strap 226, and the second end 295 of the second cuff strap 228 may attach to the second cuff strap 228 along the length 299 of the second cuff strap 228. In some embodiments, the sleeve 220 may include a first strap loop 296 and a second strap loop 297. The first and second strap loops 296, 297 may be used to maintain the first and second cuff straps 226, 228 in position. In some embodiments, the first and second strap loops 296, 297 may allow first and second cuff straps 226, 228 to fold back and be reattached along the lengths 298, 299 of the first and second cuff straps 226, 228 respectively.

In some embodiments, the first and second cuff straps 226, 228 may be made from material that is elastic and can expand or contract in response to tension on the first and second cuff straps 226, 228. For example, the first and second cuff straps 226, 228 may be formed from material that allows the first and second cuff straps 226, 228 to expand or contract when a user flexes or moves his or her leg. In some embodiments, the first and second cuff straps 226, 228 may be formed from material that does not expand or contract, but remains at a predetermined length or size. The first and second cuff straps 226, 228 may be formed from nylon, polyurethane, neoprene, Lycra®, or any other suitable material.

Figure 5:
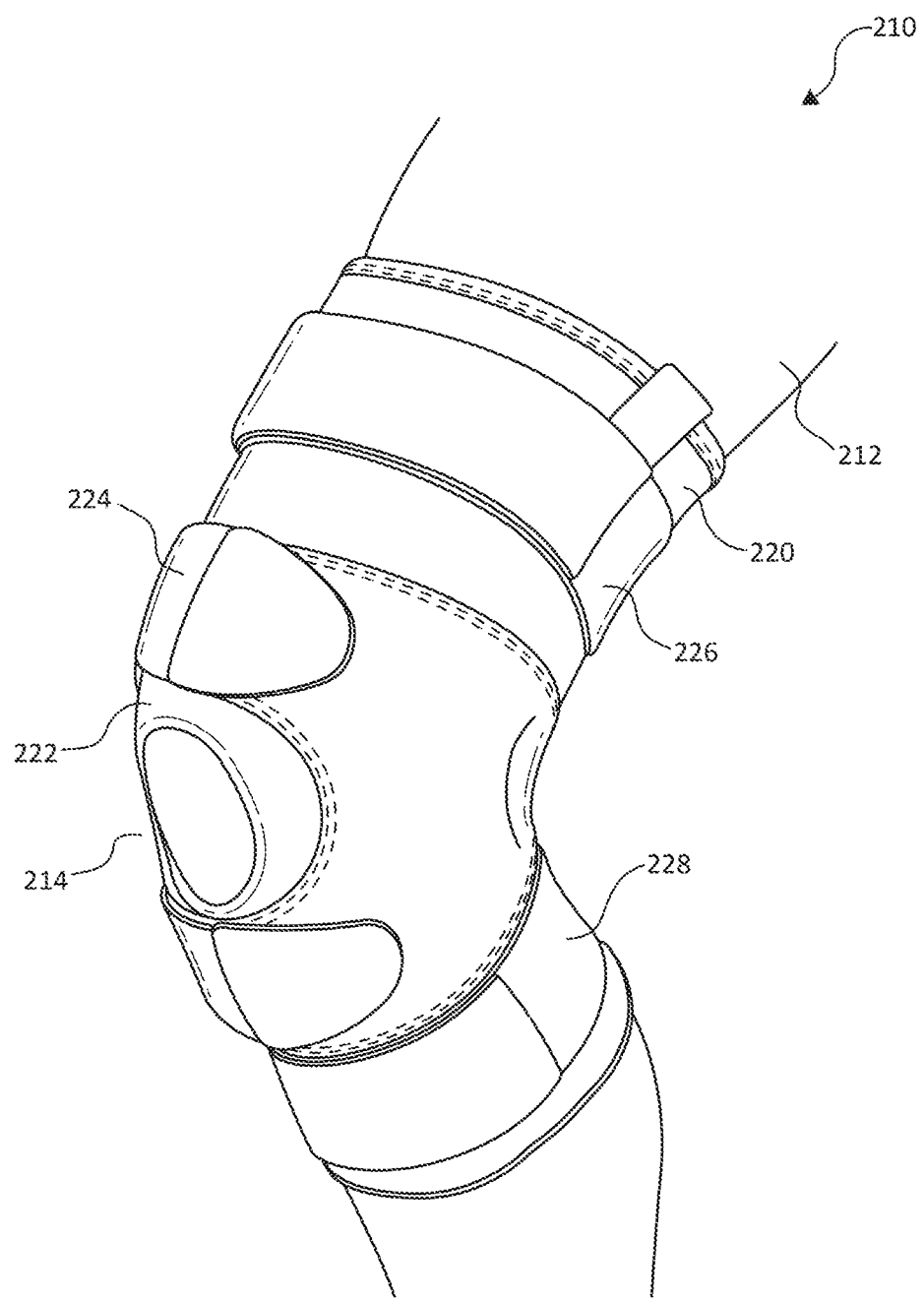
FIG. 5 is a front view of an exemplary knee brace.

FIG. 5 is a perspective view of the knee brace 210 described with reference to FIG. 4 with the knee brace 210 worn by a user, according to some embodiments. As shown in FIG. 5, the knee brace 210 includes the sleeve 220, the buttress 222 and the wrap 224. In some embodiments, the knee brace 210 may also include the first cuff strap 226 and the second cuff strap 228. In general terms, the sleeve 220 is configured to maintain the buttress 222 in position, and the wrap 224 assists with maintaining a position of the buttress 222 and provides additional support as desired. The knee brace 210 may be configured to be worn on a user's leg 212 and around a user's knee 214. The wrap 224 holds the buttress 222 against the wearer's knee 214 and provides adjustable tension to retain the buttress 222 in a desired position.

In some embodiments, the wrap 224 forms an integrated fit with the sleeve 220 and provides targeted and adjustable compression and/or support in the area of a user's patella when worn. For example, the sleeve 220 provides an inner or first support member, and may include the buttress 222 in some embodiments, and may not have a buttress in some embodiments. In embodiments both with and without a buttress 220, the shape of the wrap 224 may be used to support a user's knee and provide controllable support to the user's knee. The wrap 224 thus integrates with the sleeve 220 to provide supplemental support to the user's knee when worn. The wrap 224 may be sized and shaped to overlap with the buttress 222 and hold or cradle the buttress 222 in position adjacent a user's knee when worn. For example, the wrap 224 may be sized to cover at least a portion of the buttress 222 from the front of a user's knee with part of the wrap 224 covering around the outside of a the buttress 222. In this configuration, the wrap 224 may push the buttress 222 down over a user's knee along the outer diameter 274 of the buttress 222.

In some embodiments, an inner or first support member may be formed by the sleeve 220 having suitable structure to provide support to a user's knee without the buttress 222. That is, the sleeve 220, and the wrap 224, may work in conjunction to support the patella of a user such that the sleeve 220 forms an inner support member and the wrap 224 forms an outer or secondary support member, and the inner and outer support members provide suitable support to a user's patella.

In some embodiments, the wrap 224 provides support for maintaining the first and second brace structure 230, 232 in position adjacent a user's knee when worn. For example, the wrap 224 may form a outer or second support member that supports the first and second upper hinge stays 234, 240 and the first and second lower hinge stays 236, 242 in position adjacent the leg or joint of a user. The wrap 224 may assist in stabilizing the first and second brace structure 230, 232 in position on a user's joint and prevent the first and second brace structure 230, 232 from migrating in relation to the user's leg and/or joint.

Figure 6A:
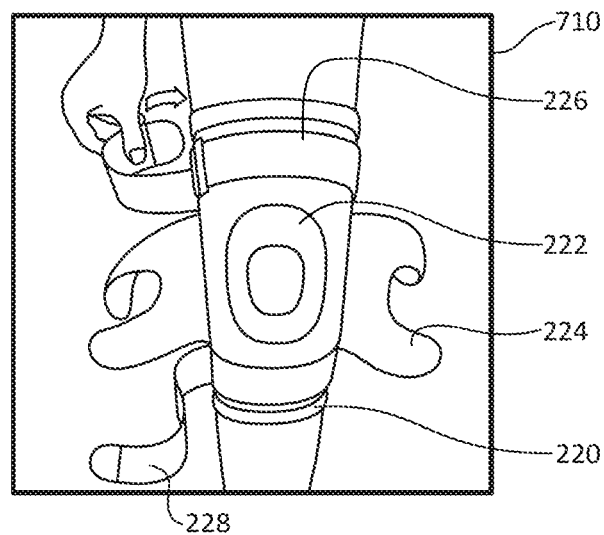
FIG. 6A-6H are perspective views of the exemplary knee brace of FIGS. 4 and 5 in various stages of fitting on a leg of a wearer.

FIGS. 6A-6H illustrate the knee brace 210 in various exemplary stages of fitting onto a leg of a user. As shown in FIG. 6A, in step 710 the sleeve 220 may be placed on a user's knee by inserting the user's leg into the sleeve 220 and advancing the sleeve 220 along the user's leg until the sleeve 220 is positioned around the user's knee. The sleeve 220 may be positioned with the buttress 222 adjacent to the user's patella. In step 710, the wrap 24 may also be positioned with at least a portion of the wrap 24 behind the user's knee. As shown in FIG. 6A the first cuff strap 226 may be positioned around the sleeve 220, for example, the first cuff strap 226 may be wrapped around the portion of the sleeve 220 that is positioned superior to the user's knee. The second cuff strap 228 may be positioned around the sleeve 220. For example, the second cuff strap 228 may be wrapped around the portion of the sleeve 220 that is positioned inferior to the user's knee.

Figure 6B:
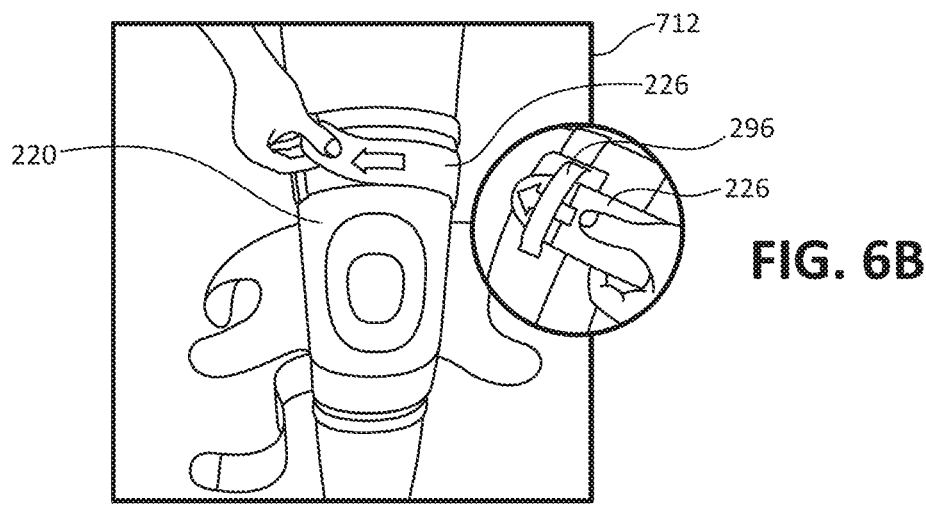

As shown in FIG. 6B, in step 712, the first cuff strap 226 may be adjusted to provide suitable compression to the user's leg by adjusting the tension in the first cuff strap 226. The tension in the first cuff strap 226 may be adjusted by inserting the first cuff strap 226 through the first strap loop 296, as shown in the insert in FIG. 6B, and folding the first cuff strap 226 back over the first strap loop 296 and attaching the first cuff strap 226 to either the sleeve 220 or the first cuff strap 226.

Figure 6C:
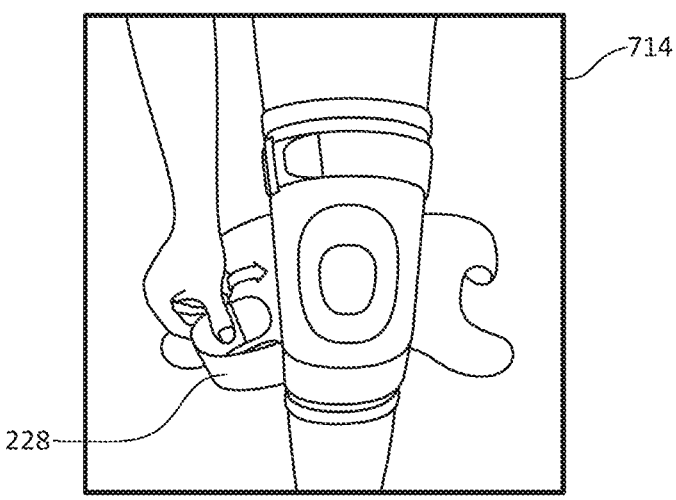
Figure 6D:
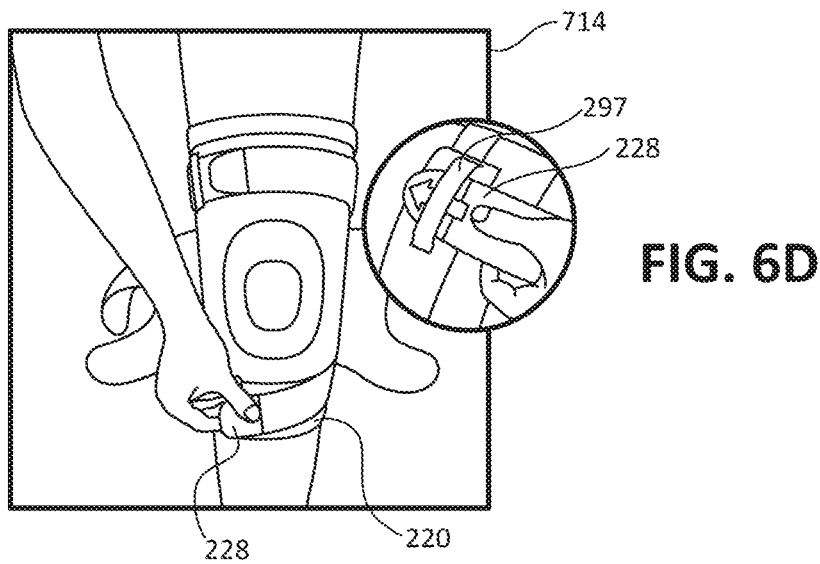

As shown in FIGS. 6C and 6D, in step 714, the second cuff strap 228 may be adjusted to provide suitable compression to the user's leg by adjusting the tension in the second cuff strap 228. As shown in FIG. 6D, the tension in the second cuff strap 228 may be adjusted by inserting the second cuff strap 228 through the second strap loop 297, as shown in the insert in FIG. 6D, and folding the second cuff strap 228 back over the second strap loop 297 and attaching the second cuff strap 228 to either the sleeve 220 or the second cuff strap 228.

Figure 6E:
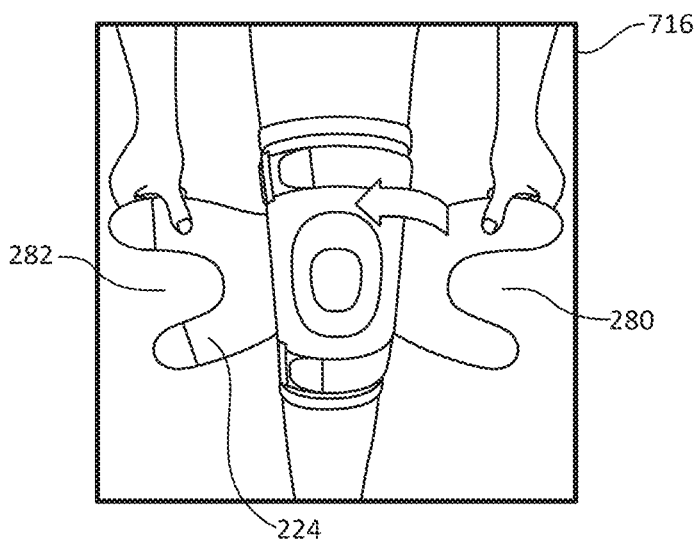
Figure 6F:
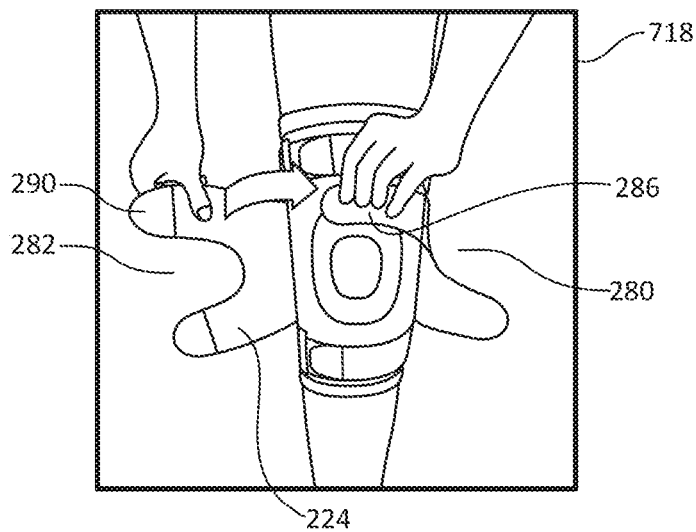
Figure 6G:
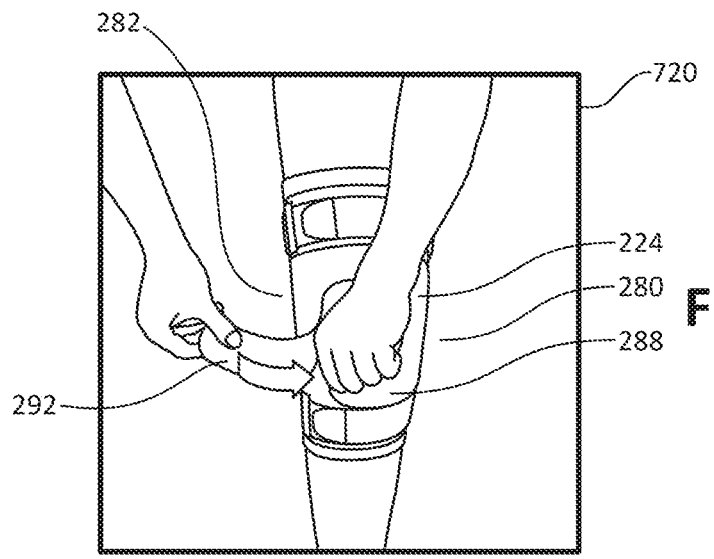

As shown in FIG. 6E, in step 716 the wrap 224 may be positioned around the user's knee with a portion of the wrap 224 behind the user's knee and the first and second ends 280, 282 of the wrap in front of the user's knee. As shown in FIGS. 6F to 6G, in step 718, the wrap 224 may be fitted around the user's knee by attaching the first end 280 to the second end 282. As shown in FIG. 6F, in step 718, the first tab 286 of the first end 280 may be attached to the first tab 290 of the second end 282. The wrap 224 may be adjusted for a suitable size or fit by adjusting the tension in the wrap 224. As shown in FIG. 6G, in step 720 the wrap 224 may be further attached around the user's knee by attaching the second tab 288 of the first end 280 to the second tab 292 of the second end 282. Note that steps 718 and 720 may be carried out in any suitable order. The wrap 224 may be adjusted for a suitable size or fit at any time by adjusting the tension in the wrap 224. The tension in the wrap 224 may be readjusted at any time by repositioning the first and second ends 280, 282 in relation to each other.

Figure 6H:
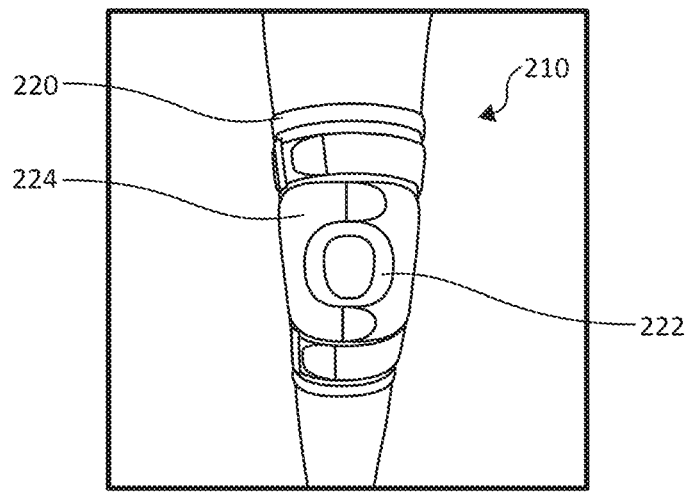

FIG. 6H is a front view showing the knee brace 210 in position on a user's knee. As shown in FIG. 6H, the brace 210 may be positioned on a user's knee with the sleeve 220 inside the wrap 224. The sleeve 220 is positioned on the user's knee and holds the buttress 222 in place adjacent to the user's knee. The wrap 224 is positioned to maintain the buttress 222 in place against the user's knee and provides supplemental support to the sleeve 220 to provide fit and tension to the user's knee. The sleeve 220 and buttress 222 form an inside support element that forms a primary support element. The wrap 224 is positioned around the sleeve 220 and buttress 222 and provides supplemental support to the user's knee by providing a compressive force inward to the buttress 222 to maintain the buttress 222 against the user's knee. The wrap 224 forms an outside support element that forms a secondary support element to the sleeve 220 and buttress 222.

Figure 7:
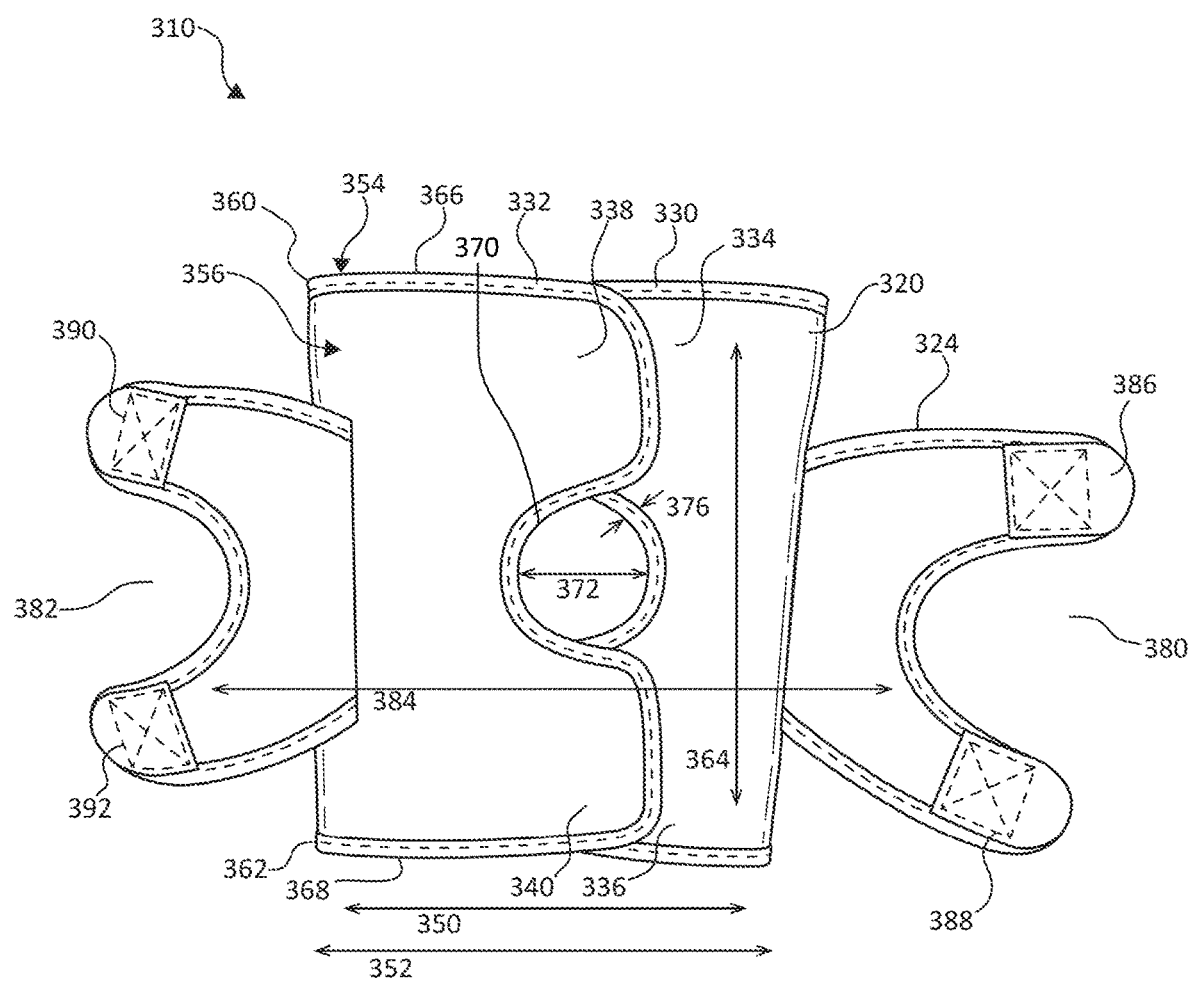
FIG. 7 is a front view of an exemplary knee brace.

FIG. 7 is a front view of an alternative embodiment of a knee brace 310. As shown in FIG. 7, the knee brace 310 includes a first support member 320 and a second support member 324. In some embodiments the first support member 320 may be positioned inside the second support member 324 to form the knee brace 310. In some embodiments, the first support member 320 may be positioned closest to the leg of a user when worn, and the second support member 324 may be placed around the first support member 320. The first support member 320 may be the primary support member or primary support element providing support to a user's leg or knee when worn, and the second support member 324 may provide additional support the first support member 320 and the leg or knee of a wearer when worn. The second support member 324 may thus function as a secondary support element or secondary support member to the first support member 320 which is the primary support member.

In some embodiments, the first support member 320 may be generally flat or planar in an open configuration. The first support member 320 may have an inner surface 354, and an outer surface 356. In general the first support member 320 may be formed as a band or wrap that may have a first end 330 and a second end 332. In some embodiments, the first support member 320 may be a suitable size for the first support member 320 to extend around the leg of a user in a plane substantially parallel the transverse plane of the body of the user and allow the first and second ends 330, 332 to meet. The first support member 320 may be configured to form a substantially U-shaped or semicircular shaped member along the first end 330 or second end 332. The first end 330 may have a first leg 334 and a second leg 336. The second end 332 may have a first leg 338 and a second leg 340. In some embodiments, the first and second legs 334, 336 of the first end 330 may be separate and unattached to each other to define a semicircular opening in between the first and second legs 334, 336. In some embodiments, the first and second legs 334, 336 of the first end 330 may be connected or joined to define a circular opening adjacent the first end 330. As shown in FIG. 7, in some embodiments, the first and second legs 338, 340 of the second end 332 may be separate and unattached to each other to define a semicircular opening in between the first and second legs 338, 340 of the second end 332. In some embodiments, the first and second legs 338, 340 of the second end 332 may be connected or joined to define a circular opening adjacent the second end 332.

As shown in FIG. 7, the first support member 320 may be configured to be attached and join with itself to form a generally cylindrical shape, shown in FIG. 7. For example, the first end 330 may be attached to the second end 332 to form a substantially cylindrical shape in a closed configuration. In a closed configuration, the first support member 320 may define a cylinder or sleeve that has a top end 360, a bottom end 362, and a length 364 in between the top and bottom ends 360, 362. As shown in FIG. 7, in a closed configuration, the top end 360 of the first support member 320 defines a first opening 366 and the bottom end 362 defines a second opening 368.

As shown in FIG. 7, the first support member 320 in a closed configuration may define a cylinder shape having an inner diameter 350 and an outer diameter 352. The inner diameter 350 of the first support member 320 may be adjustable and allow the first support member 320 to be wider or narrower at various locations along the length 364. For example, the inner diameter 350 of the first support member 320 toward the top end 360 may be sized to position a portion of the upper leg of a user, such as a thigh, when worn. The inner diameter 350 of the first support member 320 toward the bottom end 362 may be sized to receive the lower leg of a user, such as a calf or shin, when worn.

As shown in FIG. 7, in some embodiments, the first and second ends 330, 332 of the first support member 320 may be configured to join to form a generally circular or ring shaped structure. The generally circular or ring shaped structure may be configured to support a user's knee when worn. For example, first and second ends 330, 332 of the first support member 320 may be configured to join to form a support ring 370. In some embodiments, the support ring 370 may define an inner diameter 372. In some embodiments, the first and second ends 330, 332 may form a support ring 370 that defines a width 376 in a first plane around a circumference of the support ring 370.

The support ring 370 may be constructed to be overall compliant or flexible, and allow the support ring 370 to bend or conform to a suitable shape. For example, the first and second ends 330, 332 may be constructed from material that provides a resilient yet pliable support that can be shaped to support the patella of a user when worn. The first and second ends 330, 332 may include material such as rubber, plastic, foam, or any pliable material that may be used as cushioning or padding. The first and second ends 330, 332 may include a fluid or gel material, for example a gel within a bag or liner along the first and second ends 330, 332. The first and second ends 330, 332 may be made of material that forms a support ring 370 that absorbs force or shock directed at the leg or knee of a user.

In some embodiments, the first and second ends 330, 332 form a support ring 370 that has a suitable shape to provide support to the patella of a user when worn. For example, support ring 370 may be made of flexible material that can be shaped or stretched to conform to the outside surface of a user's knee. The first and second ends 330, 332 may provide support to the leg of a user when worn and maintain the support ring 370 in position along the front of the patella and against the circumference of the patella of a user in the frontal plane of the user's body. In some embodiments, the first support member 320 may be used to maintain a support structure around and in front of the patella of a user and provide comfortable support to the patella when worn by a user.

In some embodiments, the first support member 320 may be made from elastic or pliable material that can be fit snugly on a user's leg when worn. The first support member 320 may be made from material that can flex and move with a user's leg when the user runs, jumps or engages in other physical activity, yet maintains a suitable position along the wearer's leg. The first support member 320 may include material that is flexible, yet provides compression to a user's leg when worn. For example, the first support member 320 may be formed from material such as Lycra® or neoprene. The first support member 320 may be formed from material that is knit or weaved to allow breathability. The first support member 320 may be formed from material that wicks sweat or other fluids away from a user's leg when worn, and can be used to prevent the first support member 320 from building up sweat or water when worn. The first support member 320 may be made from material that provides odor absorption or odor prevention, such as material with antibacterial properties. In some embodiments, the first support member 320 may have a suitable contour or shape to fit either a user's left leg or right leg. In some embodiments, the first support member 320 may be a universal sleeve or interchangeable, i.e. the first support member 320 may be configured to be worn on either a user's left leg or right leg.

As shown in FIG. 7, the second support member 324 may have a first end 380, a second end 382, and a length 384 in between the first end 380 and the second end 382. The first end 380 may include a first tab 386, and a second tab 388. The second end 382 may include a first tab 390, and a second tab 392. The length 384 may be sized to allow the second support member 324 to extend around the leg of a user. For example, the length 384 may be a suitable size for the wrap 24 to extend in a second plane substantially parallel the transverse plane of the body of the user and allow the first and second ends 380, 382 to meet. The second support member 324 may be configured to form a substantially U-shaped or semicircular shaped member along the first end 380 or second end 382. For example, the first and second tabs 386, 388 of the first end 380 may be elongated and split the first end 380 into a U-shape, C-shape, or semicircular shape. Similarly, the first and second tabs 390, 392 of the second end 382 may be elongated and split the second end 382 into a U-shape, C-shape, or semicircular shape.

In some embodiments, the second support member 324 may be formed separate to the first support member 320. That is, the second support member 324 may combine with the first support member 320 to form the knee brace 310 by wrapping around first support member 320. In some embodiments, the second support member 324 may be attached to the first support member 320. That is the second support member 324 may be integrally formed with the first support member 320. For example, the second support member 324 may be woven through or inserted along the length 364 of the first support member 320. In some embodiments, the first support member 320 may have slots or openings along the length 364 through which the second support member 324 may be inserted, thus joining with the first support member 320 to form an integral fit with the first support member 320.

In some embodiments, the first support member 320 and second support member 324 provide targeted and adjustable compression in areas of a user's knee when worn. Using the first support member 320 and second support member 324, in conjunction, the knee brace 310 may provide controllable and adjustable support to the user's patella when worn.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the above described features.

We claim:

1. A knee brace assembly comprising:
a sleeve having a tubular shape including a first end, a second end, and a sleeve length in between the first and second end, the first end defining a first opening configured to receive a leg of a wearer, the second end defining a second opening;
a buttress attached to the sleeve and configured to be positioned against a knee of the wearer, the buttress configured to be positioned proximate a patella of the wearer and configured to provide support to the patella of the wearer; and
a wrap having a first substantially semicircular end defining an upper tab and lower tab, a second substantially semicircular end defining an upper tab and lower tab, the wrap sized to extend around the leg of the wearer, wherein the upper tab of the first substantially semicircular end is configured to attach to the upper tab of the second substantially semicircular end and wherein the lower tab of the first substantially semicircular end is configured to attach to the lower tab of the second substantially semicircular end, such that the first substantially semicircular end and the second substantially semicircular end are configured to attach to define a circular shape disposed around a circumference of the patella of the wearer in a frontal plane and the wrap is operable to form a compressive fit around the sleeve and buttress and maintain the buttress against the patella of the wearer when in use.

2. The knee brace assembly of claim 1, wherein the buttress comprises a substantially ring shaped pad configured to support the patella of the wearer.

3. The knee brace assembly of claim 1, wherein the buttress comprises a ring shaped pad with an inner circumference defining a diameter configured to receive the patella of the wearer.

4. The knee brace assembly of claim 1, wherein the buttress comprises a substantially torus shape flattened in a first plane and configured to support the patella of the wearer.

5. The knee brace assembly of claim 1, wherein the upper tab of the first end is configured to attach to the upper tab of the second end to form an upper strap positioned superior to the patella of the wearer, and wherein the lower tab of the first end is configured to attach to the lower tab of the second end to form a lower strap positioned inferior to the patella of the wearer, such that the wrap provides compression to the buttress against the patella of a user when worn.

6. The knee brace assembly of claim 1, further comprising an upper cuff strap adjacent the first opening and configured to maintain the first end of the sleeve along the leg of the wearer, and a lower cuff strap adjacent the second opening and configured to maintain the second end of the sleeve along the leg of the wearer.

7. The knee brace assembly of claim 1, wherein the sleeve is configured to provide compressive force to the leg of the wearer, the buttress is configured to provide primary support to the patella of the wearer, and the wrap provides secondary support to the patella of the wearer.

8. The knee brace assembly of claim 1, wherein the wrap is attached to the sleeve and positioned to wrap around the outside surface of the sleeve perpendicular to the sleeve length.

9. The knee brace assembly of claim 1, wherein the sleeve comprises an inner layer and an outer layer, and the buttress is positioned between the inner layer and the outer layer.

10. The knee brace assembly of claim 1, wherein the buttress is coupled to the sleeve such that inserting the leg of the wearer into the sleeve and advancing the sleeve along the leg of the wearer causes the buttress to be positioned adjacent to the patella of the wearer.

11. A knee brace for supporting a patella of a user, the knee brace comprising:
an inner support member configured to be disposed about a leg of the user, the inner support member including
a sleeve having a tubular shape including a first end, a second end, and an inner diameter sized to receive a knee of the user when worn, and
a buttress configured to be positioned adjacent the patella of the user by the sleeve when worn; and
an outer support member configured to be positioned around the inner support member and provide compression to the knee of the user when in use, the outer support member including first and second substantially semicircular ends, wherein the first and second substantially semicircular ends attach to define a circular shape configured to be disposed around a circumference of the patella of the user in a frontal plane and operating to compress the buttress against the patella of a user when worn.

12. The knee brace of claim 11, wherein the buttress is configured to be attached to the sleeve and positioned proximal to the patella of a user when worn.

13. The knee brace of claim 11, wherein the outer support member includes a wrap that is attached to the sleeve to form an integral support for maintaining the buttress against the knee of a user when worn.

14. The knee brace of claim 11, wherein the buttress is formed of a pad, cushion, foam, or a gel material.

15. The knee brace of claim 11, further comprising an upper cuff strap surrounding the sleeve and configured to maintain the first end of the sleeve along the leg of the user when worn, and a lower cuff strap surrounding the sleeve and configured to maintain the second end of the sleeve along the leg of the user when worn.

16. The knee brace of claim 11, further comprising a first and second hinge assembly, configured to be positioned on a lateral and medial side of the knee of the user when worn.

17. A knee support system comprising:
an inner support member comprising a sleeve having a tubular shape and a primary support element coupled to the sleeve, the primary support element forming a patella support configured to be positioned proximate a patella of a user and provide support to the patella of the user when worn, wherein the primary support element maintains the patella support against the patella of a user and inhibits movement of the patella in relation to the femur of a user; and an outer support member having a first substantially semicircular end defining an upper tab and lower tab, a second substantially semicircular end defining an upper tab and lower tab, and a length configured to extend around a leg of the user when worn, wherein the upper tab of the first substantially semicircular end is configured to attach to the upper tab of the second substantially semicircular end and wherein the lower tab of the first substantially semicircular end is configured to attach to the lower tab of the second substantially semicircular end, such that the first substantially semicircular end and the second substantially semicircular end are configured to attach to define a circular shape disposed around a circumference of the patella of the user in a frontal plane and the first substantially semicircular end and the second substantially semicircular end define a secondary support element configured to form an integrated support with the primary support element to support the patella of the user when worn.

18. The knee support system of claim 17, wherein the primary support element forms a substantially circular shape configured to be positioned around the circumference of the patella of the user in the frontal plane.

19. The knee support system of claim 17, wherein the patella support defines a first cavity configured to at least partially receive the patella of the user when worn.

20. The knee support system of claim 17, wherein the inner support member and outer support member are formed with an integrated fit such that the first substantially semicircular end and the second substantially semicircular end in combination provide support superior and inferior to the patella of the user when worn.

21. The knee support system of claim 17, wherein the inner support member is configured to surround the knee of the user and defines a first opening to receive the patella of the user when worn, and the second substantially semicircular end is configured to form an integral fit with the first substantially semicircular end and provide the circular shape with a second opening to support the first opening against the patella of the user when worn.

\* \* \* \* \*